United States Patent [19]

Haga et al.

[11] Patent Number: 4,929,729
[45] Date of Patent: May 29, 1990

[54] PROCESS FOR PRODUCING 2-AMINO-4,6-DICHLOROPYRIMIDINE

[75] Inventors: Takahiro Haga; Yasuhiro Tsujii; Tatsuo Isogai; Shigeo Murai; Toshihiro Tanaka, all of Kusatsu, Japan

[73] Assignee: Ishihara Sangyo Kaisha Ltd., Osaka, Japan

[21] Appl. No.: 304,031

[22] Filed: Jan. 31, 1989

[30] Foreign Application Priority Data

Feb. 19, 1988 [JP] Japan .................................. 63-37023

[51] Int. Cl.$^5$ ........................ C07D 239/42; C07F 9/65
[52] U.S. Cl. .................................... 544/330; 544/243
[58] Field of Search ................................ 544/330, 243

[56] References Cited

U.S. PATENT DOCUMENTS 3,991,190 11/1976 Garzia et al. ....................... 424/251

FOREIGN PATENT DOCUMENTS 156781 6/1988 Japan .

OTHER PUBLICATIONS

Chem. Berichte, vol. 36, No. 1 (1903), p. 2229.
The Journal of the American Chemical Society, vol. 73, pp. 3011–3012 (1951) in p. 3012 (Langerman et al.).
The Chemistry of Heterocyclic Compounds "Pyrimidines", (D. J. Brown) pp. 162–164 (1962).

Primary Examiner—John M. Ford
Attorney, Agent, or Firm—Oblon, Spivak, McClelland, Maier & Neustadt

[57] ABSTRACT

The present invention relates to an industrially advantageous process for producing 2-amino-4,6-dichloropyrimidine, which comprises reacting 2-amino-4,6-dihydroxypyrimidine or its salt with phosphorus oxychloride at a temperature of from 50° to 100° C. in the presence of a solvent and an acid removing agent. Further, the yield of 2-amino-4,6-dichloropyrimidine can be improved by hydrolyzing 4,6-dichloro-2-pyrimidinylphosphoramidic dichloride produced as a by-product of the chlorination reaction to form 2-amino-4,6-dichloropyrimidine. The 2-amino-4,6-dichloropyrimidine produced by the process of the present invention is useful as an intermediate for medicines and agricultural chemicals.

11 Claims, No Drawings

PROCESS FOR PRODUCING 2-AMINO-4,6-DICHLOROPYRIMIDINE

The present invention relates to an industrially advantageous process for producing 2-amino-4,6-dichloropyrimidine useful as an intermediate for medicines and agricultural chemicals.

For the production of 2-amino-4,6-dichloropyrimidine, Chemische Berichte, vol 36, No. 1, p. 2227–2235 (1903) discloses a process wherein malonylguanidine and phosphorus oxychloride are reacted under reflux (105°–110° C.), and U.S. Pat. No. 3,991,190 and Journal of the American Chemical Society, vol 73, p. 3011–3012 (1951) disclose a process wherein 2-amino-4,6-dihydroxypyrimidine and phosphorus oxychloride are reacted under reflux (105°–110° C.) in the presence of dimethylaniline.

However, in such conventional processes, large amounts of many by-products are formed, and the yield of the desired 2 amino-4,6-dichloropyrimidine is low. Therefore, their improvements have been desired.

The present inventors have found that the desired product can be produced in good yield and in good purity by conducting the chlorination reaction in such conventional processes at a temperature of from 50° to 100° C. by means of a solvent, and further by hydrolyzing a by-product formed by the chlorination reaction. The present invention has been accomplished on the basis of this discovery.

The present invention provides a process for producing 2-amino 4,6-dichloropyrimidine (hereinafter referred to simply as ADCP), which comprises reacting 2-amino-4,6-dihydroxypyrimidine or its salt (hereinafter referred to simply as ADHP) with phosphorus oxychloride at a temperature of from 50° to 100° C. in the presence of a solvent and an acid removing agent.

Further, the present invention provides a process for producing ADCP, which comprises the above chlorination reaction and hydrolysis of 4,6-dichloro-2-pyrimidinylphosphoramidic dichloride (hereinafter referred to simply as PPA) formed as a by-product by the chlorination reaction, to form ADCP, whereby the yield of ADCP can be improved.

Now, the present invention will be described in further detail with reference to the preferred embodiments.

In the operation of the process of the present invention, it is essential to mix ADHP, phosphorus oxychloride and the solvent and to conduct the chlorination reaction of ADHP (first step) at a temperature of from 50° to 100° C. in the presence of an acid removing agent.

Firstly, the chlorination reaction of the first step will be described.

As the salt of 2-amino-4,6-dihydroxypyrimidine to be used in the present invention, a salt of an alkali metal or alkaline earth metal such as sodium, potassium or calcium may be mentioned. In the process of the present invention, it is preferred to use such a salt.

Any solvent may be used as the solvent in the present invention, so long as it is inert to phosphorus oxychloride. Specifically, however, nitriles such as acetonitrile, propionitrile and benzonitrile; aliphatic hydrocarbons which may be substituted by halogen atoms, such as chloroform, carbon tetrachloride, ethylene dichloride, 1,1-dichloropropane, butyl chloride, n-amyl chloride, n-hexyl chloride, hexane, hexene, heptane, heptene, octane and octene; aromatic hydrocarbons which may be substituted by halogen atoms and/or alkyl groups, such as benzene, chlorobenezene, dichlorobenzene, toluene and xylene; esters such as methyl acetate, ethyl acetate or butyl acetate; and ethers such as dibutyl ether, butyl ethyl ether, diphenyl ether and dioxane, may be mentioned. Among them, nitriles and aliphatic hydrocarbons which may be substituted by halogen atoms are preferred as the solvent. A nitrile or a halogen-substituted aliphatic hydrocarbon is more preferred. Acetonitrile or ethylene dichloride is most preferred.

As the acid removing agent in the present invention, any agent may be employed so long as it is capable of removing HCl produced as a by product during the chlorination reaction of the first step, without hindering the chlorination reaction of ADHP with phosphorus oxychloride and the hydrolysis of PPA. Specifically, the acid removing agent may be a basic substance, an inert gas or air. When an inert gas or air is employed, such a gas or air is blown into the reactor to discharge HCl from the reaction system. As the acid removing agent, a basic substance is preferred among them. The basic substance includes amines such as triethylamine, diethylamine, monochloroamine, ammonia, N,N-dimethylaniline and N,N-diethylaniline; and pyridines such as pyridine, picoline and lutidine. Among them, triethylamine is most preferred.

The amounts of the reactants, solvent and the basic substance as the acid removing agent, can not generally be defined because they varies depending upon the reaction conditions. However, it is usual to employ from 1 to 7 mols, preferably from 1.5 to 4 mols, of phosphorus oxychloride, from 100 to 2,000 ml, preferably from 200 to 800 ml, of the solvent and from 0.1 to 3 mols, preferably from 0.25 to 1 mol, of the basic substance, per mol of ADHP. If the amounts are outside the above ranges, there will be drawbacks such that the reaction tends to be slow, the process tends to be less economical, or the reaction operation tends to be troublesome.

The chlorination reaction of the present invention is conducted usually at a temperature of from 50° to 100° C., preferably from 70° to 90° C., usually for a period of from 0.5 to 10 hours. If the reaction temperature is outside the above range, the reaction tends to be slow, the process tends to be less economical, or by-products which are hardly separable tend to form in a substantial amount.

The chlorination reaction product may be subjected to separation of ADCP, if necessary. However, it is usual that the product is subjected to the hydrolysis of the second step.

Now, the hydrolysis of PPA of the second step will be described.

In the hydrolysis of the present invention, the hydrolytic reaction (second step) is conducted by introducing into water the reaction product of the chlorination reaction of the first step.

The reaction product formed by the chlorination reaction of the first step of the present invention usually contains ADCP as the desired product, PPA as the main by product, unreacted phosphorus oxychloride and the solvent. The unreacted phosphorus oxychloride may be recovered from the reaction product by distillation under reduced pressure. However, without conducting such distillation under reduced pressure, this reaction product may be put into water to conduct the hydrolytic reaction of PPA. This hydrolytic reaction is a reaction for forming ADCP, phosphoric acid and hydrochloric acid by the hydrolysis of PPA. Even when phosphorus oxychloride is distilled under reduced pressure from the chlorination reaction product, it is usual that a small amount of phosphorus oxychloride still remains. Therefore, when the chlorination reaction product is mixed with water, phosphorus oxychloride and water are and to form acidic substances such as phosphoric acid and hydrochloric acid, whereby the hydrolytic reaction of PPA as the main by-product is facilitated. In this hydrolytic reaction, PPA in the reaction product is converted to the desired ADCP, while ADCP is not substantially decomposed. Therefore the hydrolysis contributes to the improvement of the yield and purity of ADCP.

The hydrolytic reaction of the present invention is conducted usually at a temperature from 30° to 70° C., preferably from 40° to 60° C. for from 0.5 to 12 hours. If the reaction temperature is outside the above range, there will be difficulties such that the reaction tends to be slow, the process tends to be less economical, or the desired ADCP tends to undergo hydrolysis, thus leading to deterioration in the yield and purity of ADCP. When a basic substance is used as the acid removing agent, a small amount of the basic substance usually remains in the chlorination reaction product. However such a basic substance does not substantially affect the hydrolytic reaction.

The solvent used in the chlorination step in the present invention may be recovered after the chlorination reaction prior to the hydrolytic reaction. However, it may be recovered after the completion of the hydrolysis. After the completion of the hydrolysis, the obtained slurry is subjected to filtration, washing with water and drying in a usual manner to readily obtain ADCP.

ADCP obtained by the process of the present invention can be reacted with e.g. an alkali metal methoxide by a usual method in the presence of a proper solvent to obtain 2-amino-4,6-dimethoxypyrimidine in good yield and in high purity.

The process of the present invention is industrially advantageous not only because ADCP can be obtained in good yield in high purity by supressing the formation of by products, and by converting PPA as the main by-product to ADCP, but also because it has the following advantages from the viewpoint of the reaction operation and the after work-up operation.

(1) By using the solvent in the chlorination reaction, the amount of phosphorus oxychloride which is relatively expensive and difficult to handle can be reduced. Further, the recovery operation of unreacted phosphorus oxychloride can be omitted or simplified.

(2) By using the solvent in the chlorination reaction, it is possible to avoid a problem of clogging, with a salt, of the dropping inlet for a basic substance when the basic substance is employed as the acid removing agent.

(3) By using the solvent in the chlorination reaction, the control of the optimum temperature for the chlorination reaction can easily be conducted, whereby formation of by-products which are hardly separable, can be supressed, and a cumbersome purification operation can be omitted.

(4) The solvent used for the chlorination reaction can be recovered by a usual simple method.

Now, the present invention will be described with reference to Examples. However, it should be understood that the present invention is by no means restricted by these specific Examples.

EXAMPLE 1

Chlorination reaction

Into a 500 ml four-necked flask equipped with a stirrer, a thermometer, a condenser and a dropping funnel, 100 ml of ethylene dichloride and 95.9 g of phosphorus oxychloride (POCl3), and 48.7 g of sodium 2-amino-4,6-dihydroxypyrimidine (SDHP) containing 23.5% of sodium chloride was introduced at room temperature. The mixture was heated to 82° C., and 25.3 g of triethylamine and 24 ml of ethylene dichloride were dropwise added over a period of 60 minutes. Then, the mixture was reacted under reflux (82°–84° C.) for 2 hours. The reaction product was analyzed by liquid chromatography and was found to contain 73.4% of 2-amino-4,6-dichloropyrimidine and 20.4% of 4,6-dichloro 2-pyrimidinylphosphoramidic dichloride and others.

Hydrolytic reaction

The reaction product obtained in the first chlorination reaction was cooled and poured into 400 ml of ice water. The mixture was stirred at 50° C. for 3 hours for hydrolysis, and the obtained slurry was subjected to filtration. From the filtrate, 99 ml of ethylene dichloride was recovered. On the other hand, the cake obtained by the filtration was washed with water and dried to obtain 33.7 g (yield: 82.2%, purity: 91.5%) of 2-amino-4,6-dichloropyrimidine.

EXAMPLE 2

Chlorination reaction

Into a 500 ml four-necked flask equipped with a stirrer, a thermometer, a condenser and a dropping funnel, 80 ml of acetonitrile and 76.8 g of phosphorus oxychloride (POCl3) were charged, and 40.3 g of sodium 2-amino-4,6-dihydroxypyrimidine containing 26.0% of sodium chloride was introduced at room temperature. The mixture was heated to 78° C., and 15.2 g of triethylamine was dropwise added over a period of 1 hour and 20 minutes. Then, the mixture was reacted under reflux (78°–82° C.) for 1.5 hours. After completion of the reaction, acetonitrile and excess phosphorus oxychloride were recovered by distillation under reduced pressure (recovered amount of acetonitrile: 71.8 ml, and recovered amount of phosphorus oxychloride: 13.7 g). The reaction product was analyzed by liquid chromatography and found to contain 69.2% of 2-amino-4,6-dichloropyrimidine, and 22.7% of 4,6-dichloro 2-pyrimidinylphosphoramidic dichloride and others.

Hydrolytic reaction

The residue of the distillation under reduced pressure of the chlorination reaction of the first step was cooled, and 360 ml of ice water was added thereto. The mixture was stirred at a temperature of from 45° to 50° C. for 3 hours for hydrolysis. The obtained slurry was subjected to filtration. The cake obtained by the filtration was washed with water and dried to obtain 27.3 g (yield: 83.2%, purity 92.4%) of 2-amino-4,6-dichloropyrimidine.

EXAMPLE 3

Chlorination reaction

Into a 100 ml four-necked flask equipped with a stirrer, a thermometer, a condenser and a dropping funnel, 20 ml of acetonitrile and 19.2 g of phosphorus oxychloride (POCl3) were charged, and 9.8 g of sodium 2-amino-4,6-dihydroxypyrimidine (SDHP) containing 23.7% of sodium chloride was introduced at room temperature. The mixture was heated to 78° C., and then 5.05 g of triethylamine was dropwise added over a period of 35 minutes. Then, the mixture was reacted under reflux (78°–82° C.) for 2.5 hours. After completion of the reaction, acetonitrile and excess phosphorus oxychloride were recovered by distillation under reduced pressure. The reaction product was analyzed by liquid chromatography and found to contain 61.9% of 2-amino-4,6-dichloropyridine and 30.4% of 4,6-dichloro-2-pyrimidinylphosphoramidic dichloride and others.

Hydrolytic reaction

The residue obtained from the chlorination reaction in the first step was cooled, and 90 ml of ice water was added thereto. The mixture was stirred at 50° C. for 3 hours. The obtained slurry was subjected to filtration, and the cake thereby obtained was washed with water and dried to obtain 6.9 g (yield: 84.2%, purity: 94.8%) of 2-amino-4,6-dichloropyrimidine.

EXAMPLE 4

7.0 g (yield: 85.3%, purity: 93.6%) of 2-amino-4,6-dichloropyrimidine was prepared in the same manner as in Example 3 except that the starting material was changed to 2-amino-4,6-dihydroxypyrimidine and the chlorination reaction time was changed to 5 hours.

EXAMPLE 5

6.30 g (yield: 76.8%, purity: 85.9%) of 2-amino-4,6-dichloropyrimidine was prepared in the same manner as in Example 3 except that no triethylamine was used, the chlorination reaction time was changed to 4 hours and nitrogen gas was continuously introduced into the reactor during the reaction.

EXAMPLES 6 to 14

The chlorination and hydrolysis were conducted in the same manner as in Example 3, whereby the following results were obtained. In Table 1, the reaction condition is the condition for the chlorination reaction, and the reaction condition for the hydrolysis was the same as the reaction condition for the hydrolysis in Example 3. Further, the amount obtained and the yield in Table 1 are of the product of the hydrolysis.

TABLE 1

| Example No. | SDHP g | POCl3 g | Solvent ml | Basic substance g | Reaction condition °C. | Reaction condition hrs | Amount obtained g | Yield % (purity %) |
|---|---|---|---|---|---|---|---|---|
| 6 | 10.1 | 11.5 | Cl-Φ 20 | Et3N 5.05 | 80–85 | 2.5 | 6.42 | 78.3 (87.2) |
| 7 | " | 19.2 | Cl-Φ 20 | Et3N 5.05 | 100 | 1.5 | 7.45 | 90.9 (83.1) |
| 8 | 99.4 | 191.9 | EDC 200 | Et3N 50.5 EDC 100 ml | Reflux temp. (82–84) | 3 | 71.2 | 86.8 (92.3) |
| 9 | 9.8 | 19.2 | CH3CN 20 | Et3N 2.5 | Reflux temp. (82) | 3.5 | 7.05 | 86.0 (86.4) |
| 10 | 15.2 | 28.9 | CH3CN 45 | NH3 0.85 | Reflux temp. (82) | 4.5 | 10.0 | 81.3 (88.8) |
| 11 | 10.1 | 19.2 | CH3CN 20 | DMA 6.1 | Reflux temp. (82) | 2.5 | 6.95 | 84.8 (87.6) |
| 12 | 9.3 | " | Dioxane 20 | Et3N 5.05 | 80–85 | 3 | 6.48 | 79.0 (85.4) |
| 13 | " | " | AcOEt 20 | Et3N 5.05 | Reflux temp. (78) | 3 | 6.82 | 83.2 (84.5) |
| 14 | " | " | n-Butyl ether 20 | Et3N 5.05 | 80–85 | 2.5 | 6.22 | 75.9 (86.6) |
| 15 | " | " | n-Hexane 20 | Et3N 5.05 | Reflux temp. (67–73) | 2.5 | 6.15 | 75.0 (91.8) |

Notes:
Cl-Φ: Chlorobenzene
EDC: Ethylene dichloride
AcOEt: Ethyl acetate
Et3N: Triethylamine
DMA: N,N-Dimethylaniline

We claim:

1. A process for producing 2-amino-4,6-dichloropyrimidine, which comprises reacting 2-amino-4,6-dihydroxypyrimidine or its salt with phosphorus oxychloride at a temperature of from 50° to 100° C. in the presence of a solvent and an acid removing agent.

2. A process for producing 2-amino-4,6-dichloropyrimidine, which comprises reacting 2-amino-4,6-dihydroxypyrimidine or its salt with phosphorus oxychloride at a temperature of from 50° to 100° C. in the presence of a solvent and an acid removing agent to form 2-amino-4,6-dichloropyrimidine and 4,6-dichloro-2-pyrimidinylphosphoramidic dichloride, and hydrolyzing the 4,6-dichloro-2-pyrimidinylphosphoramidic dichloride to form 2-amino-4,6-dichloropyrimidine.

3. The process according to claim 1, wherein a salt of 2-amino-4,6-dihydroxypyrimidine is used as the starting material.

4. The process according to claim 1, wherein the reaction is conducted at a temperature of from 70° to 90° C.

5. The process according to claim 1, wherein the phosphorus oxychloride is used in an amount of from 1 to 7 mols per mol of the 2-amino-4,6-dihydroxypyrimidine or its salt.

6. The process according to claim 1, wherein the solvent is at least one member selected from the group consisting nitriles, aliphatic hydrocarbons which may be substituted by halogen atoms, aromatic hydrocarbons which may be substituted by halogen atoms and/or alkyl groups, esters and ethers.

7. The process according to claim 1, wherein the solvent is a nitrile or a halogen-substituted aliphatic hydrocarbon.

8. The process according to claim 1, wherein the acid removing agent is at least one member selected from the group consisting of a basic substance, an inert gas and air.

9. The process according to claim 1, wherein the acid removing agent is a basic substance.

10. The process according to claim 1, wherein the acid removing agent is triethylamine.

11. The process according to claim 2, wherein the hydrolysis is conducted at a temperature of from 30° to 70° C.

* * * * *